United States Patent [19]

Fassett et al.

[11] Patent Number: 5,080,769
[45] Date of Patent: Jan. 14, 1992

[54] ELECTROPHORESIS WITH ELECTRODE BAFFLES

[75] Inventors: John R. Fassett, Irvine; Jeffrey R. Moritz, Diamond Bar, both of Calif.

[73] Assignee: Beckman Instruments, Inc., Fullerton, Calif.

[21] Appl. No.: 581,607

[22] Filed: Sep. 12, 1990

[51] Int. Cl.$^5$ .................... B01D 57/02; B01D 61/42
[52] U.S. Cl. ................ 204/180.1; 204/299 R; 204/182.8; 204/183.1
[58] Field of Search .............. 204/182.8, 183.1, 299 R

[56] References Cited

U.S. PATENT DOCUMENTS

| | | | |
|---|---|---|---|
| 4,148,703 | 4/1979 | Trop et al. | 204/299 R |
| 4,456,513 | 6/1984 | Kawai et al. | 204/299 R |
| 4,473,452 | 9/1984 | Cantor et al. | 264/182.8 |
| 4,680,103 | 7/1987 | Solomon et al. | 204/299 R |
| 4,740,283 | 4/1988 | Laas et al. | 204/182.8 |
| 4,865,715 | 9/1989 | Hellman | 204/299 R |

OTHER PUBLICATIONS

Beckman Instruments, Inc.'s Brochure No. SB-705A, "GeneLine TM".
Publication by William H. Hayt, Jr., "Engineering Electromagnetics", pp. 169-181.

*Primary Examiner*—John Niebling
*Assistant Examiner*—Caroline Koestner
*Attorney, Agent, or Firm*—William H. May; Paul R. Harder; Wen Liu

[57] ABSTRACT

A electrophoretic system in which nonconductive members are strategically positioned in the electrolyte tank to selectively affect the electric field of electrodes so as to obtain a desired electric field for efficient separation. The size, shape and location of the nonconductive members are selected using a electric potential analysis.

18 Claims, 6 Drawing Sheets

ELECTROPHORESIS WITH ELECTRODE BAFFLES

BACKGROUND OF THE INVENTION

1. Field of the Invention

The present invention relates to electrophoresis, and more particularly, to the structure of the electrolyte tank of an electrophoretic system.

2. Description of the Related Arts

Electrophoresis is a technique by which articles such as mixtures of macromolecules are moved through a separation medium by an electric field. It is a widely used technique for quantitative analysis and for separation, recovery and purification of certain macromolecular species. It is widely used for the study of proteins, nucleic acids and chromosomes.

U.S. Pat. No. 4,740,283 to Laas et al is incorporated by reference herein. The patent describes a transverse alternating field gel electrophoretic system in which a free-standing gel slab is subject to alternating electric fields oriented diagonally across the thickness of the gel slab. The alternating fields are oriented at angle ("reorientation angle") with respect to each other and cause the molecules to migrate down the gel slab in a generally saw-tooth manner oscillating within the thickness of the gel slab. The amount of migration is determined in part by the electrical charges on the particles in the sample substance, the size of the particles and the magnitude of the imposed electrical potential. Particles with similar mobilities tend to group into defined areas and thus a determination can be made as to the relative sizes of each group of particles present in the sample. At the end of the separation process, groups of particles of different mobilities are aligned along the path of migration i.e. separation lanes of the particles. Typically, several samples are processed at the same time thus forming several separation lanes in the gel slab.

The theory behind transverse alternating field electrophoresis is that separation of the sample particles can be achieved by reorientation of the particles as they migrate down the gel slab, smaller particles being able to reorient themselves faster than larger particles. Reorientation occurs each time the electric field is switched between the two transverse pairs of electrodes. It has been found that transverse alternating fields result in better resolution especially in the separation of large DNA fragments greater than 50,000 base pairs.

It has been found that the reorientation angle, defined by the angle between the original direction of migration in one instance and the reoriented direction in the next instance, i.e. the angle between the transverse directions of the alternating fields, can affect the separation efficiency. Since the migrations of the particles follow the electric field, the placement of the electrodes with respect to the gel slab can have a significant effect on the reorientation angle and thus the efficiency of the electrophoretic separation.

SUMMARY OF THE INVENTION

The present invention is directed to a means of modifying the electric fields in an electrophoretic separation tank to optimize separation efficiency. Nonconductive members are positioned in the electrophoretic tank to modify the electric fields created by the electrodes so as to obtain electric fields that will optimize electrophoretic separation. In one aspect of the present invention, nonconductive baffles are strategically positioned between the gel slab and the electrodes so as to cause the transverse electric fields across the thickness of the gel slab to be at a desired angle and magnitude and thus to obtain the desired effect. In another aspect of the present invention the optimum location of the baffles in the electrophoretic separation tank are determined from electrical potential analysis.

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

Figure 1A:
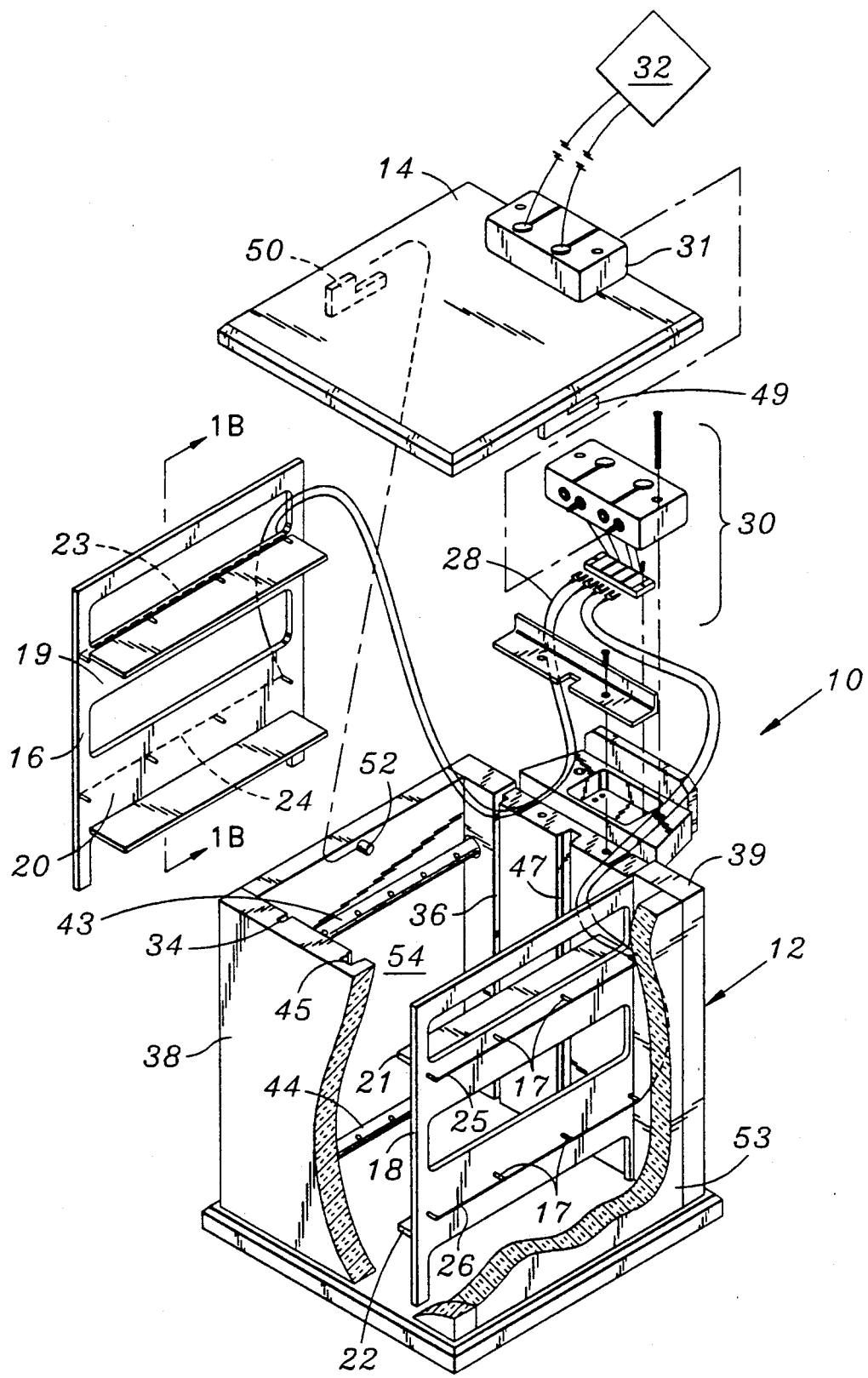
FIG. 1A is a perspective view partially broken away showing the assembly of the components of the electrolyte tank assembly in accordance with one embodiment of the present invention.
Figure 2A:
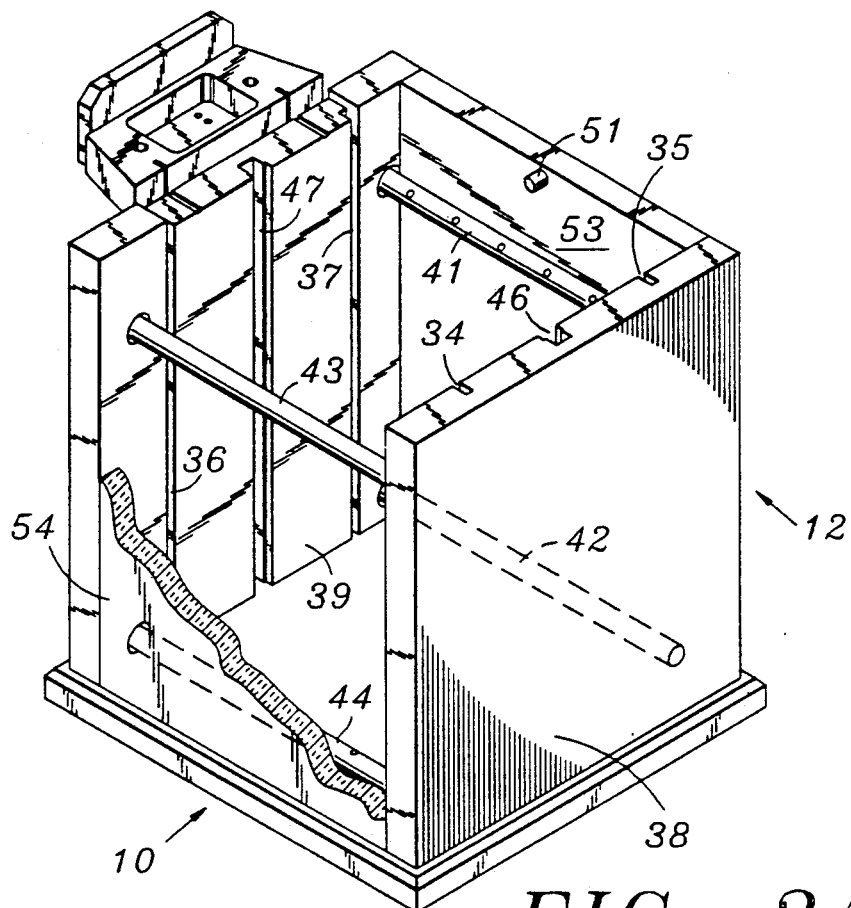
FIG. 2A is another perspective view partially broken away which more clearly shows the interior of the electrolyte tank without the baffles and electrodes.
Figures 1B, 2B:
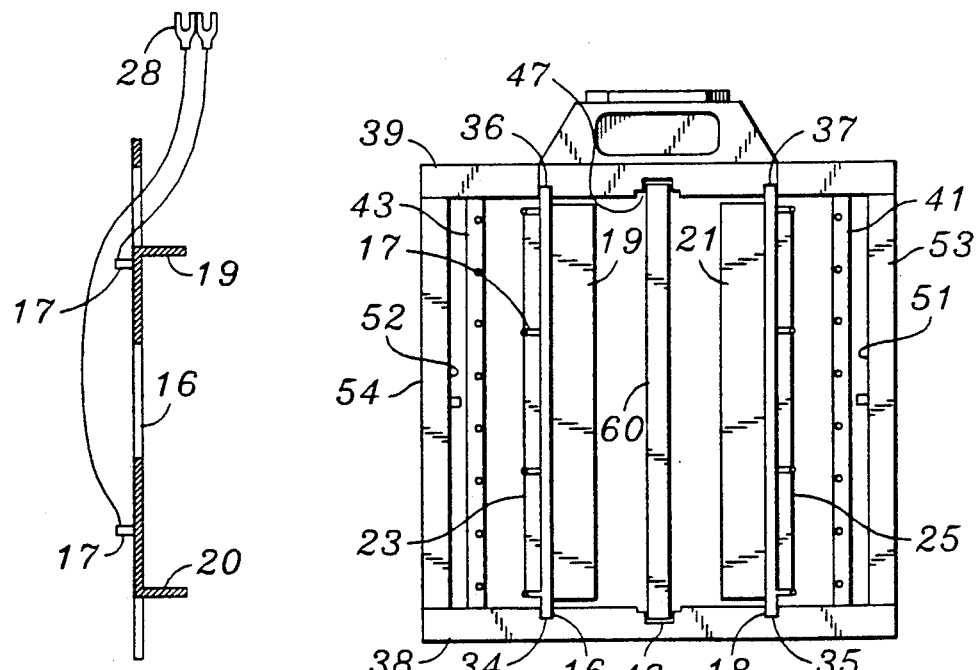
FIG. 1B is a sectional view of the baffle frame taken along line 1B—1B in FIG. 1A.
FIG. 2B is a top view of the tank in FIG. 2A with baffles and electrodes.

FIGS. 1 and 2 show a tank assembly 10 in accordance with one embodiment of the present invention. The tank assembly 10 comprises a nonconductive rectangular tank 12 for holding electrolyte; a cover 14; frames 16 and 18 for supporting nonconductive members in the form of baffles 19, 20, 21 and 22 and electrodes 23, 24, 25 and 26; leads 28 for making electrical connections; and connectors 30 and 31 for coupling to an external power supply and controller 32. The frames 16 and 18 are supported in the electrolyte tank along channels 34, 35, 36 and 37 provided in the opposing walls 38 and 39 of the tank 12. The channels 34, 35, 36 and 37 can be more clearly seen in FIGS. 2A and B. The baffles have L-shaped cross-sections as can be seen in FIG. 1B. The electrodes 23, 24, 25 and 26 extend across the tank 12 and are supported on posts 17 extending from the vertical portions of the L-shaped baffles such that when the frames 16, 17 supporting baffles 19, 20, 21 and 22 are assembled into the tank 12, the electrodes are located on the sides of the baffles away from the center of the tank. The configuration of the electrodes and baffles is more clearly shown in FIG. 2B and 3. The frames 16 and 18 are positioned symmetrically about the center of the tank at which the gel slab 60 is placed. (The gel slab 60 is omitted from FIGS. 1 and 2A for clarity.) The frames including the baffles should be made of nonconductive materials such as acrylic. The insulated leads 28 connects the electrodes 23, 24, 25 and 26 to the power distribution connector 30. In this particular embodiment, electrodes 23 and 25 are designated negative electrodes and electrodes 24 and 26 are designated positive electrodes.

In operation, a transverse pair of positive and negative electrodes are turned on for a period of time and the other transverse pair of electrodes are alternately turned on after the first pair has been turned off. The electric field thus alternates between the two pairs of diagonally opposing electrodes. This method of electrophoresis is conventional and has been described in the Laas patent.

Four tubes 41, 42, 43 and 44 with holes provided thereon circulates electrolyte in the tank. Specifically, electrolyte is pumped into the tank through the upper tubes 41 and 43 and withdrawn from the tank through the lower tubes 42 and 44. The electrolyte is cooled and circulated back into the tank 12 by an external heat exchanger (not shown). Along the center of the walls 38 and 39, channels 46 and 47 are provided for receiving and vertically supporting a gel slab 60 which may be supported and reinforced by a frame. The cover 14 has a connector block 31 attached to the upper surface for coupling an external power supply and controller 32 to the electrical connectors 30 and 31. On the under side of the cover 14, two L-shaped latches 49 and 50 are provided which are designed to latch on retaining pins 51 and 52 at the top inside wall 53 and 54 of the tank 12. To cover the tank 12, the cover 14 is lowered onto the top edge of the tank 12 and slid horizontally to electrically couple connectors 30 and 31 while the latches 49 and 50 engages the retaining pins 51 and 52 to thereby securely hold the cover 14 against the top of the tank 12.

Figure 3:
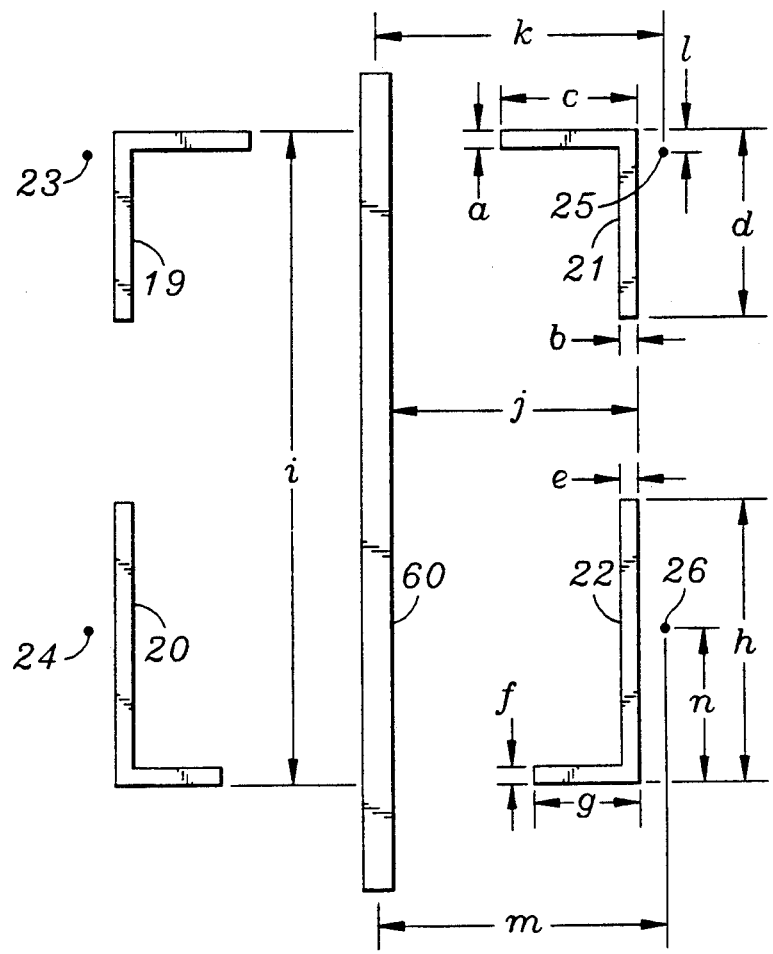
FIG. 3 is a two-dimensional view showing the relative positions of the baffles, electrodes and gel slab.

Referring to FIG. 3, the relative locations of the baffles 19, 20, 21 and 22, electrodes 23, 24, 25 and 26 and gel slab 60 are more clearly shown in two-dimension. The dimensions of the baffles 19, 20, 21 and 22 and the relative positions of the baffles, electrodes 23, 24, 25 and 26 and the gel slab 60 of a prototype are given below in reference to FIG. 3.

TABLE OF DIMENSIONS (in inches)

a = 0.125
b = 0.125
c = 1.15
d = 1.35
e = 0.125
f = 0.125
g = 0.75
h = 2.15
i = 5.0
j = 2.0
k = 2.2
l = 0.2
m = 2.2
n = 1.2

Figure 4:
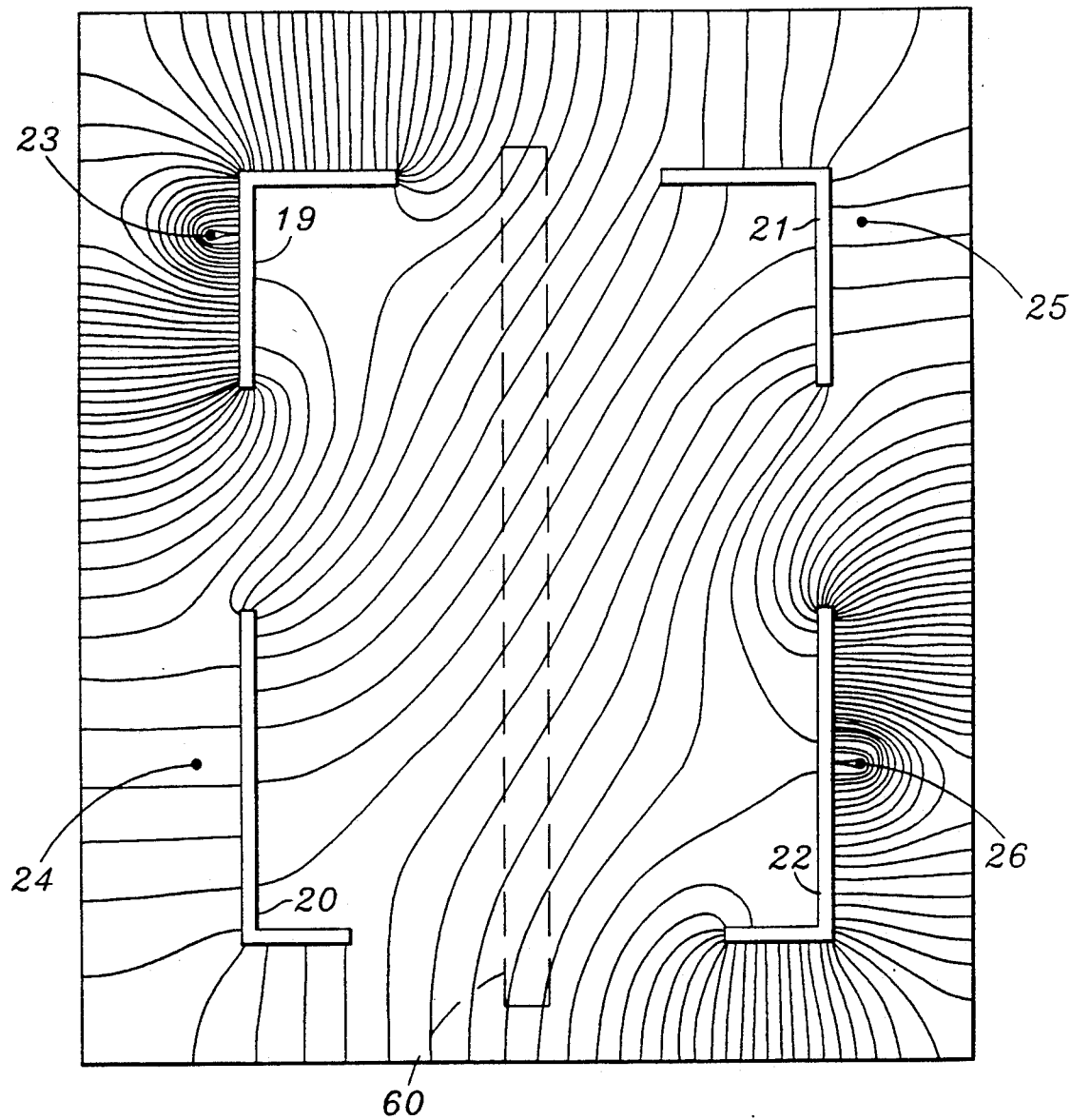
FIG. 4 is a plot of electrical equipotential lines in the presence of electrode baffles in the electrolyte tank when one pair of electrodes are energized.

Shown in FIG. 4 are the electrical equipotential lines 62 obtained by computer simulation for the configuration shown in FIG. 3 at an instance when one pair of transversely opposing electrodes are energized. The equipotential lines are obtained as a result of potential analysis by computer simulation which will be described later on. In the particular instance as shown in FIG. 4, electrodes 23 and 26 are energized. Each equipotential line represents a trace of points of equal potential. The electric field lines will be perpendicular to the potential lines. Since the design of the baffles is accomplished by electrical potential analysis as will be described below, only the equipotential lines are indicated in FIG. 4. The electric field lines can be constructed by simply considering the perpendiculars along the equipotential lines 62. The equipotential lines will follow a mirror image of what is shown in FIG. 4 upon turning on the electrodes 24 and 25 at the next instance after the first pair of electrodes 23 and 26 have been turned off.

It is noted that a nonconductive material placed in the electrolyte tank will have no electric field or current crossing through the material. Therefore, the equipotential lines at the surfaces of the nonconductive structures such as the baffles will be perpendicular to the surfaces as is the result shown in FIG. 4. Accordingly, it can be appreciated that the addition of nonconductive structures in the tank 12 and their positions relative to the electrodes will have a significant effect on the resultant electric fields. To a good assumption, the presence of the gel slab does not appreciably affect the field lines as its conductivity is similar to that of the buffer.

Figure 6:
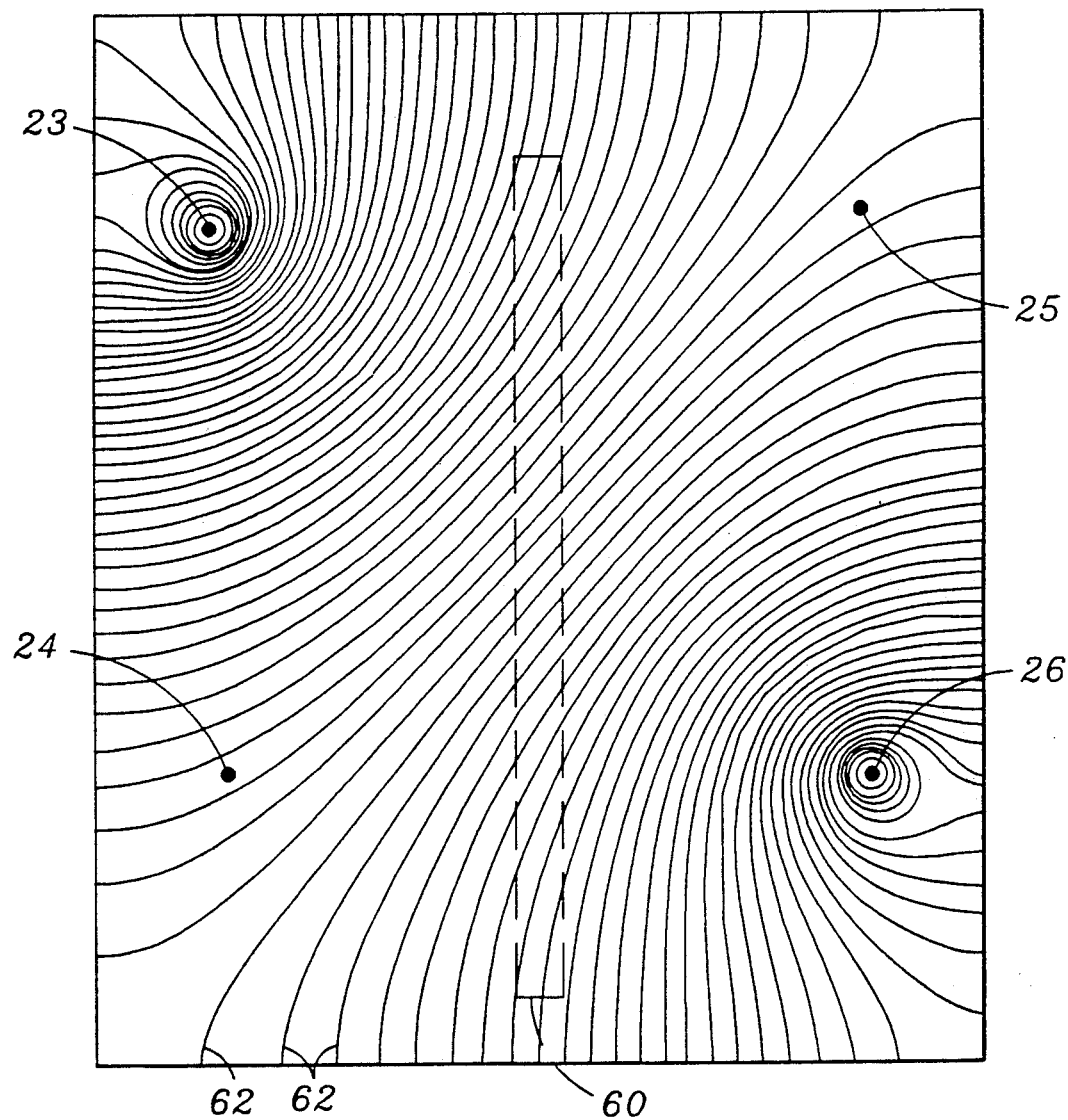
FIG. 6 is a plot of electrical equipotential lines in the absence of baffles in the electrolyte tank.
Figure 5A:
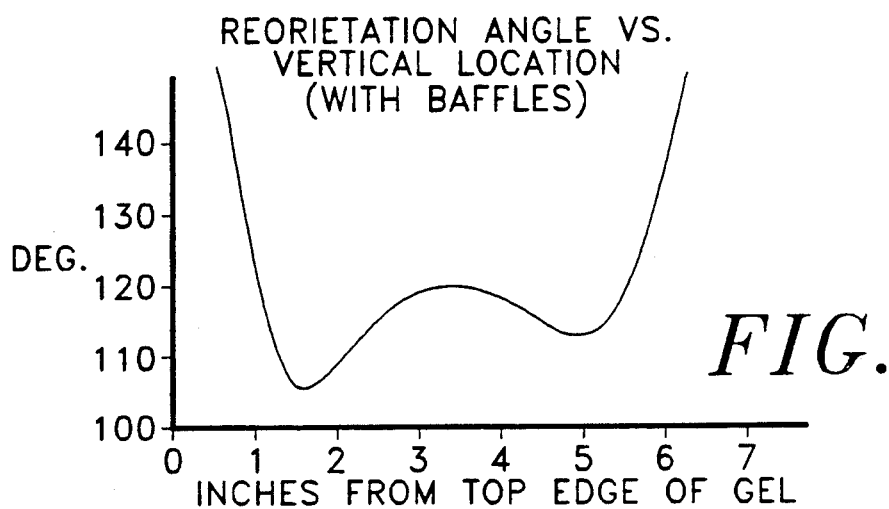
FIG. 5A is a graph of the reorientation angle versus vertical locations along the gel slab in the presence of baffles.
Figure 7A:
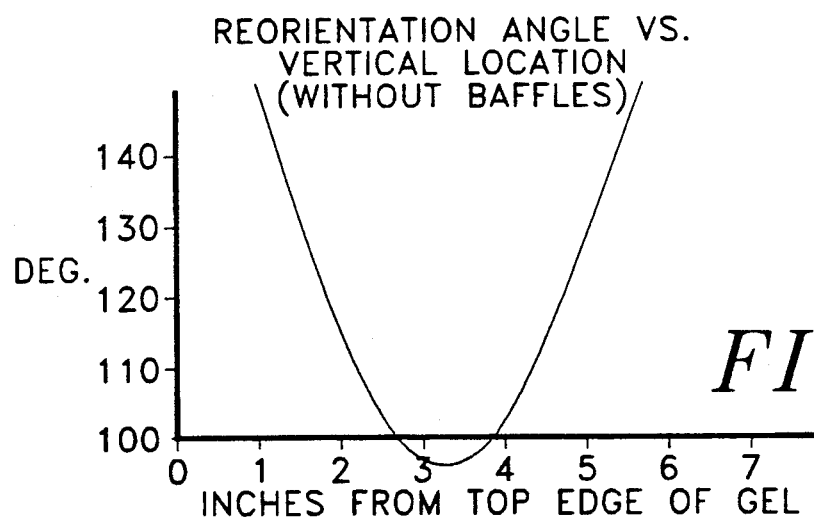
FIG. 7A is a graph of the reorientation angle versus vertical locations along the gel slab in the absence of baffles.

FIG. 5A is a plot of the reorientation angle at different vertical locations (measured from top edge of gel slab) along the gel slab. The reorientation angle is the angle between the transverse directions of the electric field lines. It has been determined that reorientation angles between 100–120° are most efficient for electrophoretic separation of most samples. Thus, according to FIG. 5A, there is approximately 5 inches of desirable and efficient field region along the separation path in the gel slab. The result has been compared to a system having the same electrode configuration but without electrode baffles. FIG. 6 is a plot of the electric equipotential lines of a pair of electrodes wherein baffles are not present. Referring to FIG. 7A, the reorientation angle is within the 100–120° range for a smaller region vertically along the gel slab. Therefore, the system according to the present invention which uses electrode baffles to alter the electric fields has efficient separation region larger than that of the system not using baffles. Comparing FIGS. 5A and 7A, the improvement is approximately a factor of 1.5.

Figure 5B:
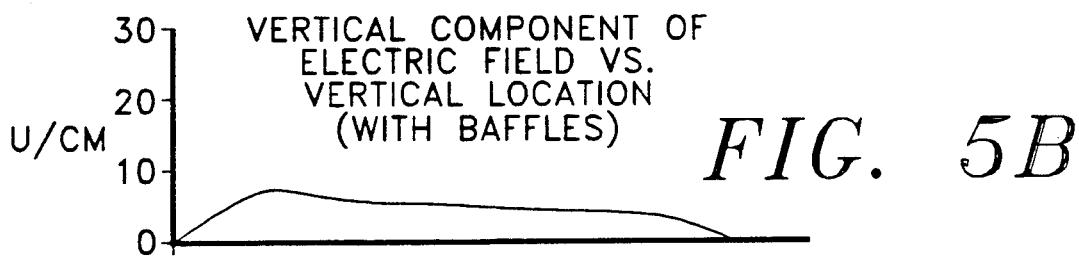
FIG. 5B is a graph of the magnitude of vertical component the electric field versus vertical locations along the gel slab.
Figure 7B:
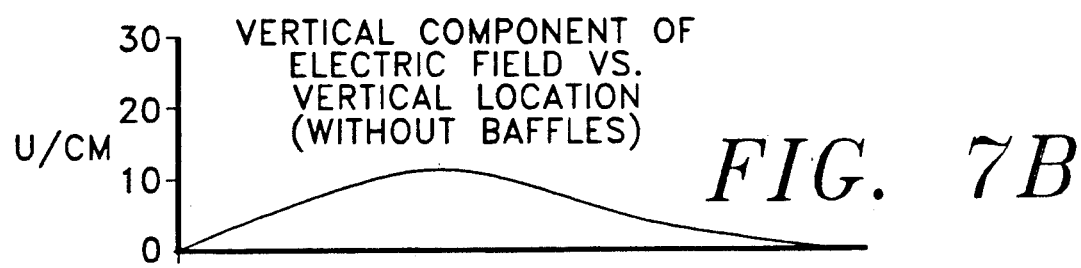
FIG. 7B is a graph of the vertical component of the electric field versus vertical locations along the gel slab in the absence of baffles.

FIGS. 5B and 7B show the plot of vertical electric field component versus vertical location (measured from top edge of gel slab) along the gel slab for the present system with baffles and conventional system without baffle, respectively. The vertical electric field component along the vertical gel slab is at a maximum at the point at which the samples are loaded (i.e., the starting point of the run) near the top edge of the gel slab and decreases in the direction of movement (i.e., downward). This gradual decrease or negative slope of the vertical component of the electric field is a key factor in the improved band sharpness and resolution of bands obtainable with this system over existing systems.

It can be appreciated that a compact electrophoretic tank can be used in accordance with the present invention without compromising separation efficiency. Without the electrode baffles, the horizontal spacings of the electrodes have to be larger in order to be able to obtain a large reorientation angle over a large gel area. It has been found that the volume of the electrophoretic tank has been reduced by approximately a factor of two over that of the tanks used in prior art systems such as the GeneLine TM electrophoresis system marketed by Beckman Instruments, Inc. which was designed according to the Laas patent.

The shapes, sizes and locations of the baffles and electrodes in the electrophoretic tank can be determined by trial and error with the aid of a computer program which solves the well-known Laplace equation $\nabla^2\phi=0$. The determination of potential distributions using the Laplace equation is well-known in the art as is documented in the fifth edition of Engineering Electromagnetics by William H. Hayt, Jr., pages 169–181, published by McGraw - Hill Book Company. The Hayt publication is incorporated by reference herein. It basically describes an iteration method of solving for the average potentials at several grid points using a finite element approach well-known in the art. The accuracy of the method depends on the number of grid points specified.

Figure 8:
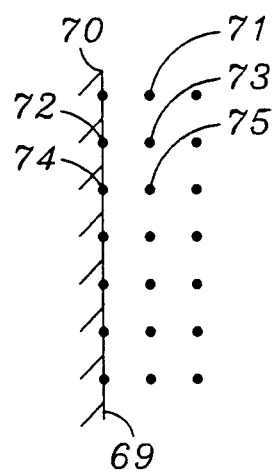
FIG. 8 illustrate the boundary conditions set forth in the electrical potential analysis for designing the baffles.

To apply the Laplace equation, appropriate boundary conditions must be applied at the surfaces of the nonconducting structures. In this case, the electric fields must not cross the boundaries defined by the nonconductive surfaces, i.e. equipotential lines must be perpendicular to the nonconductive surfaces. Thus, the analysis can be approximated by setting forth the condition that the potential at a grid point on the surface must be equal to the potential of the closest grid point along a perpendicular to the boundary surface so as to obtain zero electric fields across the boundary surface. This approach is illustrated in FIG. 8. The grid point pairs 70 and 71, 72 and 73, 74 and 75 etc. on and adjacent boundary 69 are respectively restricted to be at the same potential. Each pair, however, can have a potential different from the adjacent pair. This is consistent with the fact that electric field lines near the boundary are substantially parallel to the boundary, i.e. the potential necessarily changes along the boundary to result in such field lines. A similar approach has been practiced in the past in connection with analysis of Laplace equation for other types of physical systems including those involving temperature distribution, etc.

To a good approximation, the potential analysis is done in two-dimensions by ignoring the effect of extraneous structures on the baffle frames. The computer programming will not be discussed herein since it is merely a matter of programming skill to one skilled in the art to write a computer program for the mathematical analysis of potential distributions using the Laplace equation and the given boundary conditions. With the benefit of the discussion of the present invention herein, it is also within programming skills to design a computer program which will automatically output the configuration of the baffles and electrodes in response to an input of a specified reorientation angle. That is, by specifying the desired electric field or potential which corresponds to the desired reorientation angle, the program will work "backwards" by automatically iterating with different baffle and electrode configurations to try to match the specified result.

With the aid of computing modeling, the baffles can be sized and shaped to obtain a configuration which will produce the optimum electric fields for desired band sharpening and resolution. The effect of the baffles on the electrodes can be studied before constructing the electrophoresis system, thus saving substantial time and effort while obtaining an optimum system. Existing electrophoretic tanks of prior art designs can be modified by installing baffles designed in accordance with a computer simulation of the electrical potential fields so as to obtain the electric fields with the desired reorientation angles.

Although the system described above uses baffles at fixed predetermined locations in the electrophoretic tank, it is contemplated that the frame can be modified to support the baffles in a way which would allow them to be slid vertically and also to support the electrodes in such a way to allow them to be positioned at various vertical locations in cooperation with the baffles to produce the desired electric fields. Also, several frames having different baffle and electrode configurations can be made available corresponding to different reorientation angles, whereby one of these frames corresponding to a desired reorientation angle can be selected for use in the electrolyte tank. Furthermore, the tank can have several vertical channels to allow the frame to be inserted at various distances from the central gel slab.

The capability of "custom tailoring" the electric fields can be advantageous in some applications. For example, it may be possible to calibrate the reorientation angle with respect to sample particle sizes so as to be able to selectively separate selected components from a sample in a preparative procedure. Also, specified particles of the sample can be purified by selectively separating unwanted components. The above can be done by performing several electrophoretic separation steps in sequence using progressively larger reorientation angles obtained by modifying the electric fields in accordance with the present invention, so that smaller particles are separated first and removed until the desired particles are finally separated from the sample.

While the invention has been described with respect to the preferred embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

We claim:

1. A system for performing electrophoretic separation in a separation medium comprising:
   a tank for holding electrolyte;
   means for supporting a separation medium in the tank;
   electrode means positioned in the tank for creating an electric field for causing separation of a sample in the medium; and
   nonconductive means positioned in the tank for selectively affecting the electric field so as to obtain a desired electric field.

2. A system as in claim 1 wherein the nonconductive means is positioned between the electrode means and the separation medium.

3. A system as in claim 1 wherein the means for supporting comprises a structure which will support a gel slab type separation medium vertically in the tank.

4. A system as in claim 3 wherein the electrode means comprises at least one negative electrode which is positioned on one side of the gel slab and at least one positive electrode which is positioned on another side of the gel slab.

5. A system as in claim 4 wherein the positive and negative electrodes are so positioned as to create an electric field diagonally across the thickness of the gel slab.

6. A system as in claim 5 further comprising a frame supporting at least one of the electrodes and the nonconductive means.

7. A system as in claim 6 wherein the nonconductive means is in the form of a baffle.

8. A system as in claim 7 wherein the baffle has a L-shaped cross-section.

9. A system as in claim 1 wherein the electrode means comprises first and second pairs of positive and negative electrodes so positioned in the tank such that at a particular location along the gel slab the first pair of electrodes create an electric field across the thickness of the gel in a first direction and the second pair of electrodes create a electric field across the thickness of the gel in a second direction, and wherein the system further comprising means for energizing the first and second pairs of electrodes in sequence.

10. A system as in claim 9 wherein the difference in the first and second directions defines a reorientation angle, and wherein the size, shape and location of the nonconductive means are selected to obtain a desired electric field corresponding to a desired reorientation angle.

11. A system as in claim 10 wherein the nonconductive means is in the form of a baffle.

12. A method of performing electrophoretic separation comprising the steps of:
    providing a tank for holding electrolyte;
    supporting a separation medium in the tank;
    exposing the separation medium to an electric field to cause electrophoretic separation of a sample in the medium; and
    positioning nonconductive means in the tank to selectively affect the electric field so as to obtain a desired electric field.

13. A method as in claim 12 wherein further comprising the step of using computer simulation to select the size, shape and location of the nonconductive means so as to obtain the desired electric field.

14. A method as in claim 12 further comprising the step of providing electrodes for creating the electric field and wherein the nonconductive means is positioned between at least one of the electrodes and the separation medium.

15. A method as in claim 12 further comprising the step of providing first and second pairs of positive and negative electrodes, wherein the electrodes are so positioned in the tank such that at a particular location along the gel slab the first pair of electrodes create a electric field across the thickness of the gel in a first direction and the second pair of electrodes create a electric field across the thickness of the gel in a second direction, and wherein the method further comprises the step of energizing the first and second pairs of electrodes in sequence.

16. A method as in claim 15 wherein the difference in the first and second directions defines a reorientation angle, and wherein the method further comprises the step of using computer simulation to select the size, shape and location of the nonconductive means so as to obtain a desired electric field corresponding to a desired reorientation angle.

17. A method of selecting the size, shape and location of a nonconductive member which is to be positioned in an electrophoretic tank for affecting electric field created by electrodes in the electrophoretic tank so as to obtain a desired electric field, comprising the steps of:
    simulating by computer analysis the electric field created as a result of an initial chosen size, shape, and location of the nonconductive member in the tank; the electric field in the tank by computer analysis; and
    adjusting the size, shape and location of the nonconductive member and resimulating until the desired electric field has been reached.

18. A method as in claim 17 wherein the step of simulating comprises electric potential analysis involving Laplace equation.

* * * * *